United States Patent [19]

Hattori et al.

[11] 4,308,518
[45] Dec. 29, 1981

[54] GAS COMPONENT DETECTOR

[75] Inventors: Tadashi Hattori; Mitsuru Asano, both of Okazaki; Minoru Ohta, Anjo; Eturo Yasuda, Okazaki, all of Japan

[73] Assignee: Nippon Soken, Inc., Nishio, Japan

[21] Appl. No.: 167,023

[22] Filed: Jul. 9, 1980

[30] Foreign Application Priority Data

Jul. 12, 1979 [JP] Japan .................................. 54-96404

[51] Int. Cl.$^3$ ............................................. H01L 7/00
[52] U.S. Cl. ..................................... 338/34; 73/27 R; 422/98
[58] Field of Search ................. 338/34, 35; 204/192 S; 73/27 R; 340/632, 633, 634; 23/232 E; 200/61.04; 422/98, 83, 88; 318/483

[56] References Cited

U.S. PATENT DOCUMENTS

| | | | |
|---|---|---|---|
| 3,630,874 | 12/1971 | Olette et al. | 204/195 S |
| 3,704,984 | 12/1972 | Kiefer | 73/27 R |
| 3,883,408 | 5/1975 | Kim et al. | 204/195 S |
| 3,959,764 | 5/1976 | Allman | 338/34 |
| 3,959,765 | 5/1976 | Stewart | 338/34 |
| 3,978,006 | 8/1976 | Topp et al. | 204/195 S X |
| 4,007,106 | 2/1977 | Hone et al. | 204/195 S |
| 4,045,177 | 8/1977 | McNally | 338/34 X |
| 4,193,289 | 3/1980 | Springer et al. | 73/27 R |
| 4,193,857 | 3/1980 | Bannister et al. | 204/195 S |
| 4,206,173 | 6/1980 | Yamaguchi et al. | 73/27 R X |
| 4,209,378 | 6/1980 | Schinohara et al. | 204/195 S |
| 4,218,297 | 8/1980 | Henault et al. | 204/195 S |
| 4,220,517 | 9/1980 | Niwa et al. | 204/195 S |
| 4,223,293 | 9/1980 | Springer et al. | 73/27 R |

Primary Examiner—C. L. Albritton
Attorney, Agent, or Firm—Cushman, Darby & Cushman

[57] ABSTRACT

A gas component detector has a detector element of a metal oxide held on one end of a ceramic body. The detector element is electrically connected to a pair of electrodes and the pair of electrodes are in turn welded to a pair of sub-lead-lines to deliver a detected electric signal from the detector element. The pair of electrodes and sub-lead-lines are inserted in a pair of through holes of the ceramic body and the pair of electrodes are fixed by an inorganic adhesive within the through holes. The openings of the pair of through holes of the ceramic body at the opposite end with respect to the detector element are closed by a sealing material of an electrically insulating metal oxide.

6 Claims, 7 Drawing Figures

GAS COMPONENT DETECTOR

BACKGROUND OF THE INVENTION

1. Field of the Invention

The present invention relates to a gas component detector which may suitably be used in exhaust gas purifying systems employing a three-way catalyst of, for example, automobiles.

2. Description of the Prior Art

Gas component detectors known in the art include the one as disclosed in U.S. Pat. No. 3,959,765. In this case, a detector is constituted by a detector element having a sintered body of a transition metal oxide, a pair of electrodes buried in the detector element, and a ceramic body having a pair of narrow holes to accomodate therein the pair of electrodes and a pair of large penetrating holes to accomodate therein a pair of lead pins for picking up a change in electrical resistance value of the detector element to outside. An electrically conducting glass is used between the electrodes and the lead pins to obtain the electrical conduction therebetween. Further, the detector has a housing with threads to enable it to be mounted on an exhaust pipe or the like.

By further study of the gas component detectors having the construction conventionally known as mentioned above, it has been found that some problems still exist. For example, conductive glass is used to electrically connect the lead pins and the electrodes. However, since it is necessary to push in the lead pins and to apply pressure on the conductive glass when it is in a melted state for the purpose of filling the conductive glass uniformly in the connecting portion, lead pins having a large diameter must be used in order to widen an area of the lead pins to be applied with pressure. Thus, a large ceramic body is needed, and consequently, the construction of the detector itself becomes large.

Further, there are problems as mentioned below, in the gas component detector which is known from U.S. Pat. No. 4,001,758.

(1) The ceramic body and the housing are fixed by caulking using a washer and a ring. Therefore, the caulking force is apt to be insufficient, becomes loose and thus insufficiently airtight, and also sometimes the ceramic body or the detector element is broken at the time of caulking.

(2) The electrodes are not fixed in the trough holes. Therefore, the electrodes start vibrating when vibrations are transmitted to the electrode from outside. Consequently, the electrodes can be cut or broken. Also, in case the electrodes are made with a large diameter, the thickness of the detector element connected with the electrodes becomes larger and the response deteriorates.

SUMMARY OF THE INVENTION

The present invention has an object to provide a useful gas component detector capable of overcoming above-mentioned problems.

DESCRIPTION OF THE PREFERRED EMBODIMENTS

Figure 1:
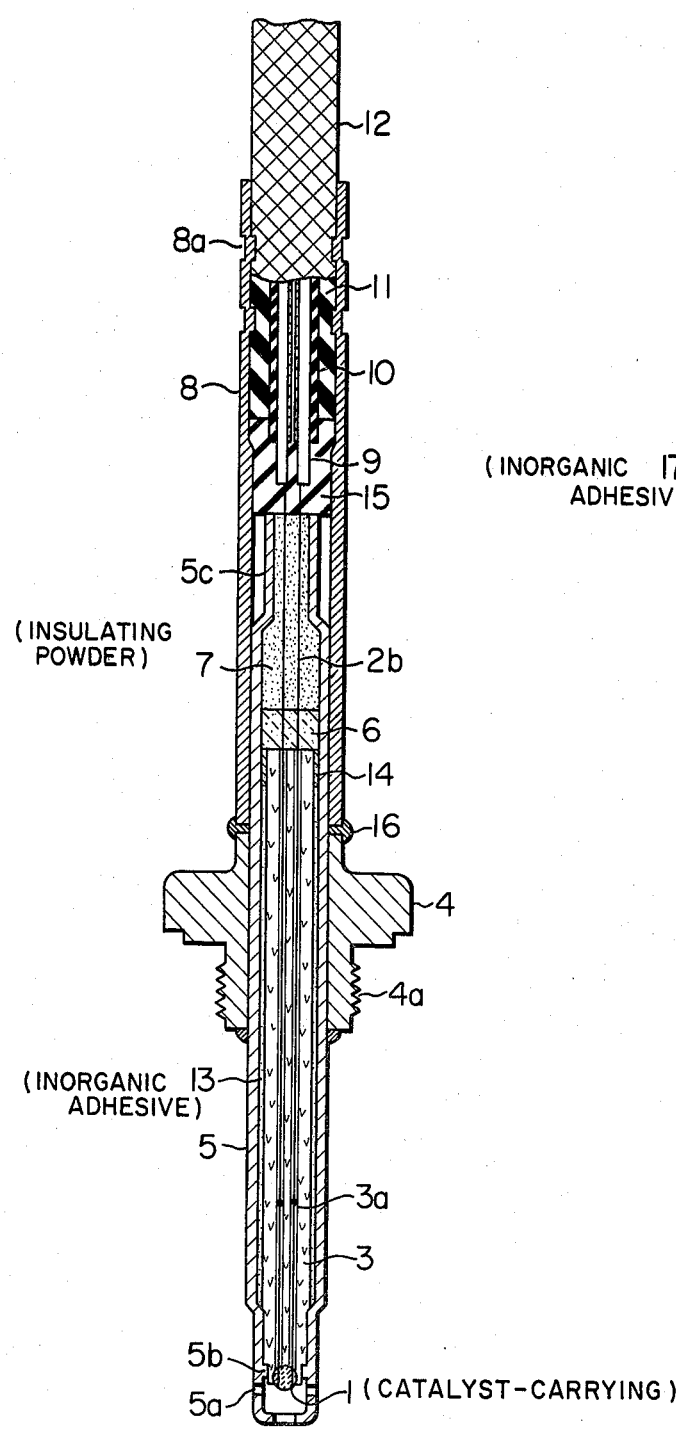
FIG. 1 is a longitudinal cross-sectional view of a gas component detector of an embodiment of this invention.
Figure 2:
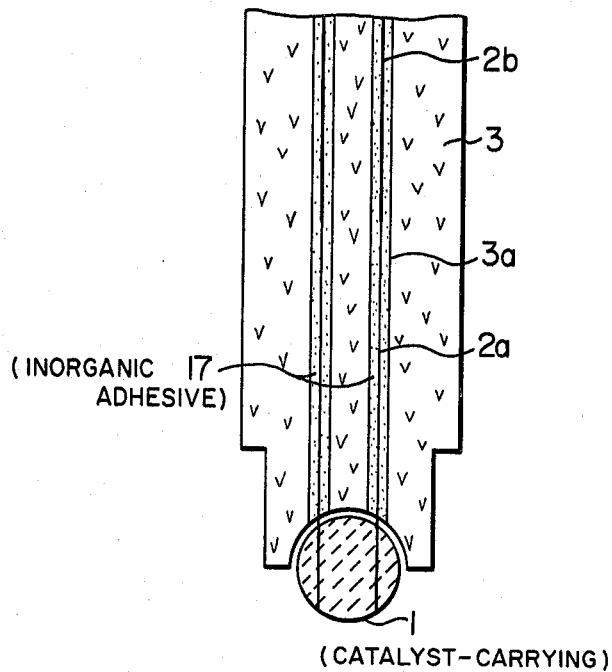
FIG. 2 is a cross-sectional view showing the main portion of FIG. 1.
Figure 3:
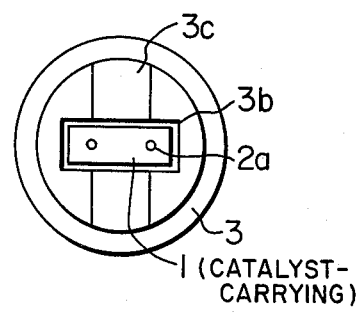
FIG. 3 is a bottom view of FIG. 2.

In FIG. 1 to FIG. 3, 1 is a detector element having a sintered body of a metal oxide such as titanium oxide, tin oxide or the like on which is carried a catalyst. As shown in FIG. 2, 2a designates a pair of electrodes made of platinum or the like which are buried in the detector element 1. 2b designates a pair of sub-lead-lines made of a heat-resistant metal such as stainless steel or the like which are welded to the electrodes 2a to provide electrical connection and conduction therebetween. 3 is a cylindrical ceramic body having a pair of narrow through holes 3a having the same diameter, and the electrodes 2a and the sub-lead-lines 2b are inserted in the through holes 3a. The ceramic body 3 has at substantially the center thereof a portion having a larger outer diameter, and the body 3 is made of heat-resistant, electrically insulating ceramic such as alumina (aluminum oxide), etc. Referring to FIG. 3, at the detector element side of the ceramic body 3, a groove 3b for supporting the detector element 1 and a groove 3c for allowing the exhaust gas to meet with the detector element 1, are provided. Again making reference to FIG. 1, 4 is a housing made of a heat-resistant metal having a thread portion 4a to be mounted on an exhaust pipe. 5 is a pipe which is made of heat-resistant metal and a plurality of holes 5a for passage of the exhaust gas are formed, and a ring-shaped projection 5b is formed at the inside bottom of the pipe 5. The above-mentioned ceramic body 3 is mounted on this projection 5b. 6 is an inorganic glass sealing material and it is filled between the ceramic body 3 and the pipe 5 to close the opening portions of the penetrating holes 3a of the ceramic body 3, and the glass sealing material 6 is in a hardened state. By this glass sealing material 6, the sealing against the exhaust gas, and the fixing and insulation of the sub-lead-lines 2b are insured. 7 designates powders of alumina, magnesia or the like and serve to fix the positions of the sub-lead-lines 2b and to maintain the electrical insulation therebetween. 8 is a pipe of a heat-resistant metal and is fixed by welding to the pipe 5. 9 designates a pair of lead lines connected to the sub-lead-lines 2b by welding and thus electrically conducting therewith. The lead lines 9 are covered by a cover 10 of a heat-resistant, electrically insulating material such as glass wool or heat-resistant rubber or the like, and, the cover 10 is also covered by another cover 11 of the same material so that the lead lines 9 are electrically insulated from each other. 12 is a cover made by knitting heat-resistant metal wires and covers the outer surface of the cover 11. This cover 12 is fixed to the pipe 8 by caulking the end of the pipe 8 as shown at 8a. Furthermore, the pipe 5 is caulked as shown at 5c at the end thereof, so that the density of the electrical insulation powder 7 filled in the pipe 5 is made high. 13 is an inorganic adhesive such as Sumiceram (trade name), etc., and it becomes hard after being poured into the gap between the ceramic body 3 and the pipe 5, and owing to this adhesive 13, the ceramic body 3 and the pipe 5 are tightly fixed. 14 is a heat-resistant metal ring used for the compression of the adhesive 13. 15 is a heat-resistant rubber such as silicon rubber or the like disposed between the pipe 5 and the outermost cover 12 of the lead lines 9, in the pipe 8. Furthermore, the pipe 8 and the housing 4 are fixed by welding at a portion shown at 16. 17 is an inorganic adhesive such as Sumiceram (trade name) etc., and it becomes hard after being poured into the gap between the penetrating holes 3a and a pair of electrodes 2a and owing to this adhesive 17, a pair of electrodes 2a are tightly fixed in position within the through holes 3a so as not to move. The adhesive 17 is poured into the penetrating holes 3a by an injector, or the electrodes 2a are inserted into the penetrating holes 3a after coating thereon, in advance, with the adhesive 17. It is preferable to pour the adhesive 17 completely over the whole length of the penetrating holes 3a, but it may be filled at least in the detector element side of the through holes 3a.

In the construction as described above, an electrical resistance value shown in the detector element 1 depending on a gas component in the exhaust gases can be picked up through the pair of electrodes 2a, the sub-lead-lines 2b and the lead lines 9. These adhesives 13, 17 are an aqueous solution of a mixture containing, for example, alumina ($Al_2O_3$), zirconia ($ZrO_2$) or silica ($SiO_2$) etc., as the main component, and primary aluminum phosphate, aluminum hydroxide, or barium carbonate, etc., as the binder, and magnesium oxide (MgO), calcium oxide (CaO), or magnesium hydroxide as the hardener. For one example, as the adhesives 13, 17, an aqueous solution containing 85% alumina, 12% primary aluminum phosphate and 3% magnesium oxide may be used.

Figure 4:
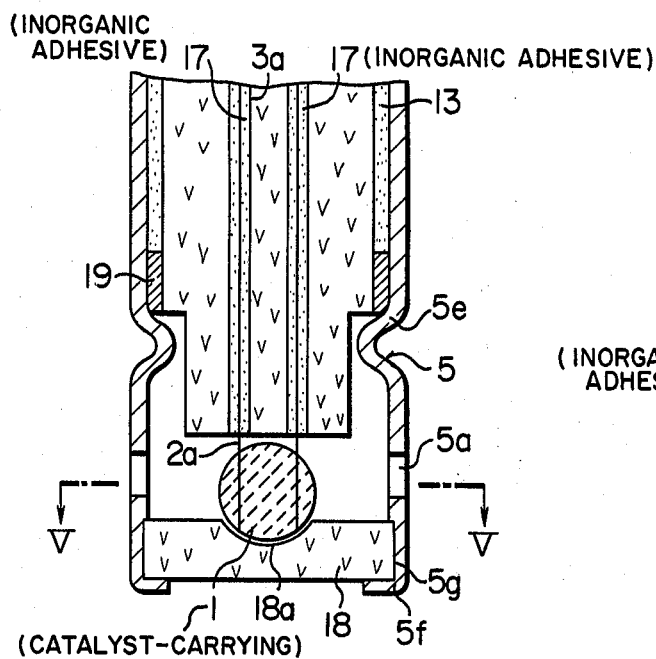
FIG. 4 is a cross-sectional view showing the main portion of another embodiment.
Figure 5:
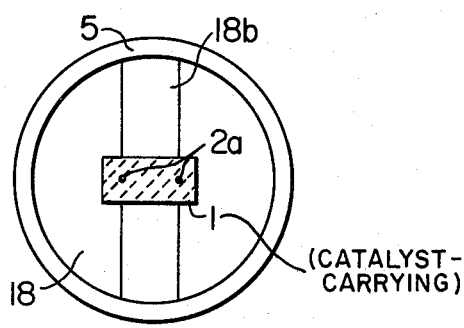
FIG. 5 is a cross-sectional view taken along the line V—V in FIG. 4.

FIG. 4 and FIG. 5 show another embodiment of this invention in which a disc-shaped heat-resistant electrically insulating body 18 is disposed in a cylindrical groove formed at the inside and bottom portion of the pipe 5. The insulating body 18 is fixed by caulking the end edge 5f of the pipe 5. The insulating body 18 is provided on a main surface with a hollow 18a for holding the detector element 1 and a groove 18b extending substantially diametrically to allow the detector element 1 to be exposed to the exhaust gas flow more completely. Further, in this embodiment, a ring-shaped caulking portion 5e is formed around the pipe 5 and the above-mentioned ceramic body 3 is mounted on a shoulder formed by the inwardly projecting ring-shaped caulking portion 5e interposing a heat-resistant metal ring 19 between the inside surface of the pipe 5 and the outside surface of the ceramic body 3. It will be apparent that the caulking portion 5e may be formed after the ceramic body 3 has been disposed inside of the pipe 5 and by caulking the side wall of the pipe 5. In accordance with this embodiment, detector element 1 can be rigidly fixed in position due to the employment of the insulating body 18, since the detector element 1 is not moved by vibration or by the flow of exhaust gases.

Figure 6:
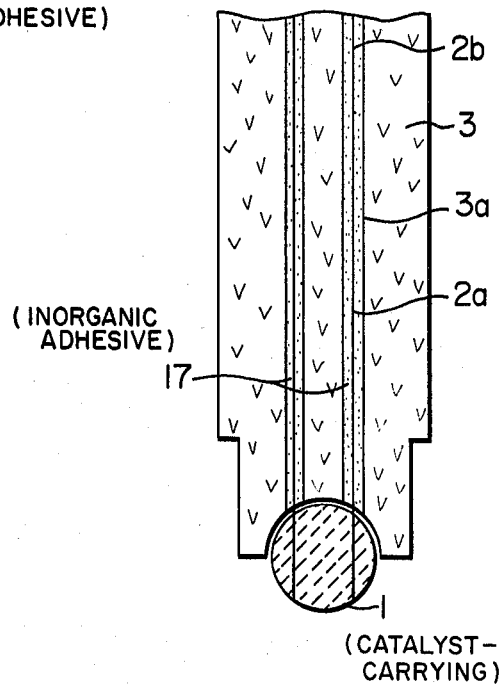
FIG. 6 is a cross-sectional view showing still another embodiment.
Figure 7:
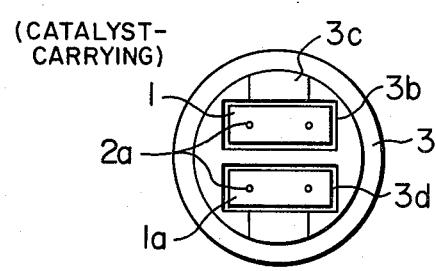
FIG. 7 is a bottom view of FIG. 6.

FIG. 6 and FIG. 7 show another embodiment of the gas component detector in which the gas component detector is temperature compensated by providing a further detector element 1a which does not carry a catalyst thereon. In this embodiment, an inorganic adhesive 17 such as Sumiceram, etc. is filled and hardened in the gap between a pair of electrodes 2a of both detector elements 1 and 1a, and through holes 3a of a ceramic body 3. Further, the detector element 1a carrying no catalyst and used for the above-mentioned temperature compensation has substantially the same temperature coefficient as the detector element 1 for detecting the gas component and is composed of the same metal oxide as the detector element 1.

This invention is not limited to the above-described embodiments and various modifications may be made, as follows.

(1) The sealing material 6 is not limited to glass, and any material may be used inasmuch as the material is an electrically insulating, heat-resistant metal oxide.

(2) The heat-resistant and electrically insulating powders 7 are not necessarily filled therein.

(3) The ceramic body 3 is fixed to the pipe 5 by the adhesive, but both members may be fixed to each other by forming respective stepped portions by bringing the surfaces of the stepped portions into contact with each other thereby eliminating the use of the adhesive 13.

(4) This invention is not limited to the usage for automobiles and can be applied to various kinds of usage.

In this invention, as described in the foregoing, the gas component detector includes an electrically insulating and heat-resistant ceramic body 3 having a pair of through holes 3a penetrating axially, a detector element 1 positioned at one end of the ceramic body 3 and composed of a metal oxide which exhibits an electrical resistance value depending on the gas component in gases to be detected, a pair of electrodes 2a connected with the detector element 1 and inserted into one end portion of the through holes 3a penetrating the ceramic body 3, a pair of sub-lead-lines 2b inserted into the other end portion of the through holes 3a penetrating the ceramic body 3 and connected by welding with the electrodes 2a, a metal pipe 5 fixed to the outer surface of the ceramic body 3 by contacting the stepped surface or fixed by an adhesive 13, and a sealing material 6 made of an electrically insulating metal oxide in a set or hardened state filled between the pipe 5 and the other end of the ceramic body 3 to close the openings of the through holes 3a at the other end thereof. And the electrodes 2a and sub-lead-lines 2b are connected by welding and they are not connected using a conductive glass as conventionally employed. Therefore, it is not necessary to use lead-pins having a large diameter for pressurizing the conductive glass. As a result, the diameters of the electrodes 2a and the sub-lead-lines 2b can be made to be small, and hence the diameter of the pair of through holes 3a of the ceramic body 3 can also be made small. Accordingly, the overall structure and size of the ceramic body 3, and also of the detector itself can be made small.

Furthermore, in this invention, the openings of the through holes 3a at the other end of the ceramic body 3 are closed by a sealing material 6 of a metal oxide in a hardened state by filling the sealing material 6 between the pipe 5 and the other end of the ceramic body 3. Therefore the present invention can resolve the problems and difficulties involving the employment of special techniques in manufacturing and in which the melting temperature or the viscosity of the conductive glass had to be considered in such a case where the conductive glass is used in both ways for sealing the through holes of the ceramic body and for connecting the electrodes to the lead pins, that is, where the conductive glass serves for sealing and for electrical connection.

In addition, since in the present invention, the pair of electrodes are by the adhesive 17 fixed in the through holes 3a of the end portion at the side of the detector element 1, the electrodes 2a are inhibited from moving and hence breakage or disconnection of the electrodes 2a are prevented thereby improving the reliability of the gas component detector.

What is claimed is:

1. A gas component detector comprising:

an electrically insulating and heat-resistant ceramic body having a pair of through holes penetrating axially;

a disc-shaped detector element of a metal oxide positioned at a first end of said ceramic body, said detector having an electrical resistance value which varies depending on a gas component in gases to be detected;

a pair of electrodes connected to said detector element and extending into said through holes at said first end of said ceramic body;

a pair of sub-lead-lines connected to said pair of electrodes by welding and extending out of said through holes and therebeyond at a second end of said ceramic body;

a metal pipe fixed to said ceramic body around an outer surface thereof by an adhesive, said pipe extending beyond said first and second ends of said ceramic body to cover the whole length thereof, the extended portion of said metal pipe beyond the second end of said ceramic body terminating in a reduced end portion;

a sealing material of an electrically insulating metal oxide filled between said second end of said ceramic body and an inner surface of said metal pipe to close openings of said through holes at said second end thereof and to fix said pair of sub-lead-lines in place in electrically insulated relationship from one another, said sealing material being in a hardened state after having been filled;

an inorganic adhesive for fixing said pair of electrodes within said through holes of said ceramic body; and a metal housing fixed on the outer surface of said metal pipe.

2. A gas component detector according to claim 1 further comprising a disc-shaped heat-resistant electrically insulating body for supporting said disc-shaped detector element, said supporting body being fixed to said first end of said metal pipe in a relation spaced from and opposed to said first end of said ceramic body to support said detector element in a space between said ceramic body and said supporting body, said supporting body having a groove on a surface supporting said detector element to lead a flow of exhaust gases to main surfaces of said detector element.

3. A gas component detector according to claim 1 wherein said disc-shaped detector element carries thereon a catalyst, said gas component detector further comprising a further detector element having no catalyst carried thereon and positioned at said first end of said ceramic body side-by-side with said first-mentioned detector element, both of said detector elements having substantially equal temperature coefficients and said further detector element being used for temperature compensation.

4. A gas component detector according to claim 1 wherein said inorganic adhesive is filled in said through holes over the whole length of said ceramic body.

5. A gas component detector according to claim 1 wherein connection points between said pair of electrodes and said pair of sub-lead-lines are held in place by said inorganic adhesive.

6. A gas component detector according to claim 1 wherein said pair of sub-lead-lines within said extended portion of said metal pipe beyond said second end of said ceramic body are fixed in place by electrically insulating powders.

* * * * *